United States Patent
Parekh et al.

(10) Patent No.: US 10,407,795 B2
(45) Date of Patent: Sep. 10, 2019

(54) ANALYSIS OF SILVER ION AND COMPLEXING AGENT IN TIN-SILVER ELECTRODEPOSITION SOLUTION

(71) Applicant: ECI Technology, Inc., Totowa, NJ (US)

(72) Inventors: Vishal Parekh, Parsippany, NJ (US); Eugene Shalyt, Washington Township, NJ (US)

(73) Assignee: ECI Technology, Inc., Totowa, NJ (US)

( * ) Notice: Subject to any disclaimer, the term of this patent is extended or adjusted under 35 U.S.C. 154(b) by 359 days.

(21) Appl. No.: 15/353,424

(22) Filed: Nov. 16, 2016

(65) Prior Publication Data

US 2018/0135199 A1      May 17, 2018

(51) Int. Cl.
| | | |
|---|---|---|
| *C25D 21/12* | (2006.01) | |
| *C25D 21/14* | (2006.01) | |
| *C25D 3/46* | (2006.01) | |
| *C25D 3/60* | (2006.01) | |

(52) U.S. Cl.
CPC .............. *C25D 21/14* (2013.01); *C25D 3/46* (2013.01); *C25D 3/60* (2013.01)

(58) Field of Classification Search
CPC ................................ C25D 21/12; C25D 21/14
See application file for complete search history.

(56) References Cited

U.S. PATENT DOCUMENTS

| | | | |
|---|---|---|---|
| 6,890,758 B2 | 5/2005 | Shalyt et al. | |
| 7,273,540 B2 | 9/2007 | Sonada et al. | |
| 8,118,988 B2 | 2/2012 | Shalyt et al. | |
| 8,920,623 B2 | 12/2014 | Luo et al. | |
| 2004/0253740 A1* | 12/2004 | Shalyt | G01N 31/164 436/124 |
| 2005/0184369 A1* | 8/2005 | Sonoda | B23K 35/262 257/677 |
| 2005/0263399 A1* | 12/2005 | Shalyt | C25D 3/38 205/82 |
| 2009/0194430 A1* | 8/2009 | Shalyt | G01N 31/164 205/788.5 |
| 2010/0035356 A1* | 2/2010 | Shalyt | C23C 18/1683 436/163 |
| 2012/0138471 A1 | 6/2012 | Mayer et al. | |
| 2013/0334052 A1 | 12/2013 | Chua et al. | |
| 2015/0267310 A1 | 9/2015 | Ikumoto et al. | |

* cited by examiner

*Primary Examiner* — Bryan D. Ripa
(74) *Attorney, Agent, or Firm* — Baker Botts L.L.P.

(57) ABSTRACT

The present disclosure relates to methods of monitoring the concentrations of silver ion and complexing agent in tin-silver (SnAg) electrodeposition solutions, and analysis and process control using such methods. Methods can include adding a precipitating agent to an electrodeposition solution including at least tin ions, silver ions, and complexing agent to cause a reaction between at least a portion of the precipitating agent and substantially all of the silver ions (to precipitate silver ions as a precipitant); adding a metallic salt to the electrodeposition solution to cause a reaction with substantially all of the remaining precipitating agent; measuring the endpoint of the silver ion back titration; further adding metallic salt to cause a further reaction with the complexing agent; and measuring the endpoint of the complexing agent titration.

10 Claims, 4 Drawing Sheets

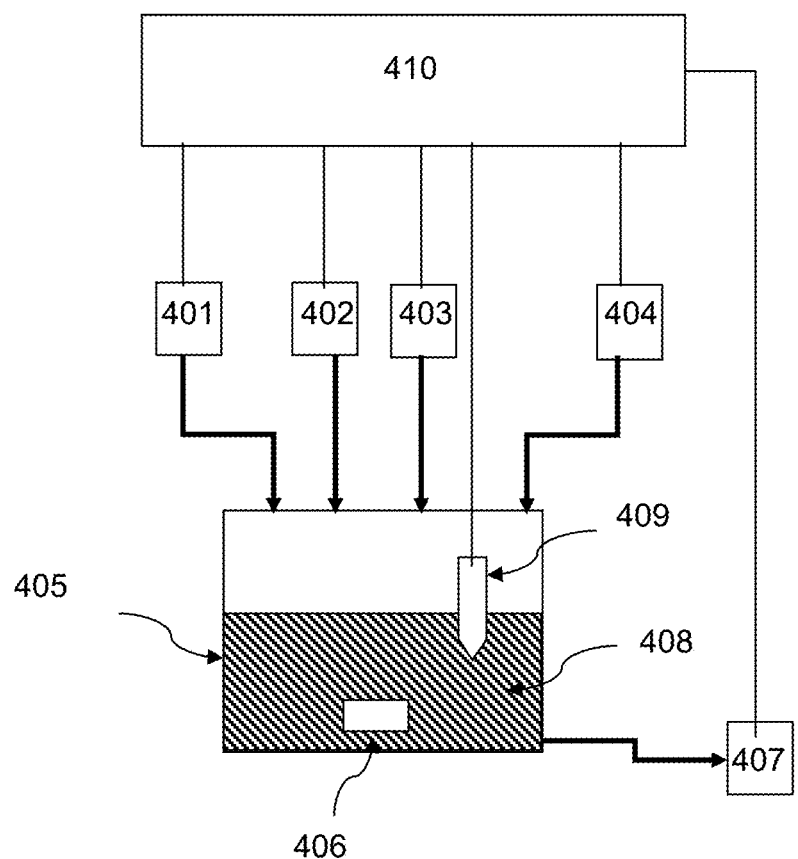

ANALYSIS OF SILVER ION AND COMPLEXING AGENT IN TIN-SILVER ELECTRODEPOSITION SOLUTION

BACKGROUND OF THE INVENTION

Field of the Invention

The present disclosure relates to methods of monitoring the concentrations of silver ion ($Ag^+$) and complexing agent in tin-silver (SnAg) electrodeposition solutions, and analysis and process control using such methods.

Description of the Related Art

Historically, certain tin-lead (SnPb) bumps were electrodeposited onto semiconductor chips to provide electrical interconnections between various circuitry elements or between integrated circuit devices. Due to environmental and health concerns related to lead (Pb), tin-silver (SnAg) was identified as an alternative electrodeposition solution material. However, certain techniques for electrodeposition of SnAg bumps have posed challenges as a result of the different chemical properties of silver as compared to lead, e.g., deposition potential, as well as their interactions with each other in a plating bath. In particular, under most conditions, silver ions ($Ag^+$) react with tin(II) ions ($Sn^{2+}$) producing an undesirable precipitant product ($SnO_2$):

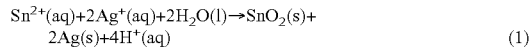

$$Sn^{2+}(aq) + 2Ag^+(aq) + 2H_2O(l) \rightarrow SnO_2(s) + 2Ag(s) + 4H^+(aq) \quad (1)$$

In order to prevent the undesirable reaction shown in equation (1), and/or to bring the reduction potential of silver closer to that of tin, a complexing agent (also referred to as a complexer or complexant) can be added to an electrodeposition solution to control the concentration of silver ions and/or allow silver to better deposit or adsorb onto the intended substrate. (For the purpose of the present disclosure, "complexing agent" and "complexer" are used interchangeably.)

Certain complexing agents that are used generally for tin or tin alloy electroplating and bump production are known in the art. For example, U.S. Patent Application Publication No. 2015/0267310 discloses a tin or tin alloy electroplating bath comprising an inorganic acid, an organic acid, and a water-soluble salt; a non-ionic surfactant; and leveling agents—with optional additive complexing agent components selected from thioamide compounds and non-aromatic thiol compounds. A preferred type of thioamide compound is thiourea.

In the deposition of SnAg bumps, both silver ions and complexing agent are consumed in the process. However, maintaining uniform manufacturing quality of integrated circuit devices can require a suitably constant composition, i.e., a suitably constant concentration, of reactants in the electrodeposition solution bath. Thus, it can be important to monitor the concentrations of silver ions and complexing agent in solution over the course of the electrodeposition process, and to do so in a safe and simple but accurate way.

Certain, existing methods have been problematic, whether due to measuring silver ion concentration, or measuring complexing agent concentration, or both.

Methods to measure silver ion concentration include atomic absorbance spectroscopy (AAS), inductively coupled plasma spectroscopy (ICP), or titration of silver ions by bringing the cation out of solution through precipitation of an insoluble product, commonly using iodide. However, certain AAS techniques require use of an open flame, which is not be suitable for use inside a semiconductor fabrication facility. ICP has the benefit of being an automated process, but it can require expensive and bulky analyzer equipment coupled with a pre-dilution system.

Methods to measure complexing agents include high performance liquid chromatography (HPLC) or titration of "free complexer," i.e., complexing agent that is not bonded to silver ions, using a silver-based titrant with a silver electrode and subsequent calculation, where the total complexing agent concentration is equal to the free complexer in solution plus the complexer amount bound to silver ions. However, HPLC can be expensive and complicated, and can require use of flammable and hazardous solvents such as methanol or acetonitrile. Measurement of the complexing agent using "free complexer" titration can require two separate analysis steps, which compounds the likelihood of error, increases overall analysis time, and consumes large amounts of chemicals.

Certain methods of electrodeposition and/or using titration to monitor concentrations of metal ions and/or complexing agent during electrodeposition are known in the art. For example, U.S. Pat. No. 6,890,758 to Shalyt et al., involves determining the concentration of citrate complexing agent in an electroless cobalt or nickel plating bath by titration with a standard lanthanum nitrate solution containing a small, predetermined concentration of free fluoride ions. U.S. Pat. No. 7,273,540 to Sonada and Nakamura, discloses an electrolytic plating method using plating solutions that include tin, copper, and silver ions, and a complexing agent. The patent discloses that control of concentrations of the metal ions in the plating solution can be achieved by volumetric techniques, such as oxidation-reduction titration, chelatometric titration, and precipitation titration.

U.S. Pat. No. 8,118,988 to Shalyt et al., teaches a simple titration method involving a single copper ion titrant to determine concentrations of both copper ions and bath complexing agent in alkaline copper electroplating baths used to deposit or thicken copper seed layers on silicon wafers. In this reference, the electrolyte is a chelated copper solution, and a chelator reagent is added before the titration analysis. U.S. Pat. No. 8,920,623 to Luo et al., discloses techniques for replenishing tin and its alloying metals in an aqueous electrolytic plating bath using an acidic solution containing stannous oxide. In one example, the patent discloses an initial tin/silver alloy electroplating composition. Silver ion concentration was analyzed by AAS, and the complexing agent-1-allyl-2-thiourea—was analyzed by reverse titration.

U.S. Patent Application Publication No. U.S. 2012/0138471 teaches an electroplating apparatus that allows for continuous simultaneous electroplating of two metals with substantially different electrodeposition potentials, such as SnAg alloys. Similarly, U.S. Patent Application Publication No. U.S. 2013/0334052 discloses an alloy plating system that performs continuous electroplating while maintaining substantially constant concentrations of plating bath components for extended periods of use. The reference states that concentration of the plating bath components can be monitored using a variety of sensors and titrations without providing details.

Thus, there remains a need for safe, simple, and inexpensive methods that accurately measure the concentrations of silver ions and complexing agent during the electrodeposition of SnAg bumps.

SUMMARY OF THE DISCLOSED SUBJECT MATTER

The disclosed subject matter provides novel techniques for monitoring the concentrations of $Ag^+$ and complexing agent in SnAg electrodeposition solution, and analysis and process control using such methods.

As embodied herein, an exemplary method of monitoring the concentrations of silver ions ($Ag^+$) and complexing agent in SnAg electrodeposition solution includes adding a precipitating agent ($X^-$) having a predetermined concentration to the electrodeposition solution to cause a reaction between at least a portion of the precipitating agent ($X^-$) and substantially all of the silver ions ($Ag^+$) such that the substantially all of silver ions ($Ag^+$) are precipitated out from the electrodeposition solution as a precipitant (AgX); adding a metallic salt ($Me^+$) of predetermined concentration to the electrodeposition solution to cause a reaction between at least a portion of the metallic salt ($Me^+$) and substantially all of the precipitating agent ($X^-$) remaining in the electrodeposition solution that did not react with the silver ions ($Ag^+$); measuring the first endpoint of the silver ion ($Ag^+$) back titration; further adding metallic salt ($Me^+$) of predetermined concentration to the electrodeposition solution to cause a reaction between at least a portion of the metallic salt ($Me^+$) and substantially all of the complexing agent in the electrodeposition solution; and measuring the second endpoint of the complexing agent titration.

In certain embodiments, the concentration of silver ions ($Ag^+$) originally in the electrodeposition solution can be calculated based on the first endpoint.

In certain embodiments, the concentration of complexing agent originally in the electrodeposition solution can be calculated based on the second endpoint.

In certain embodiments, the precipitating agent has a stronger affinity for silver ions than the complexing agent. The anion of the precipitating agent ($X^-$) can be selected from the group consisting of $Cl^-$, $Br^-$, $I^-$, $PO_4^{3-}$, $CN^-$, $C_2O_4^{2-}$, $S^{2-}$, $F^-$, $SO_4^{2-}$, $CO_3^{2-}$, or $BH_4^-$. In one embodiment, the precipitating agent can comprise potassium iodide, KI.

In certain embodiments, the cation of the metallic salt ($Me^+$) is selected from Ag, Fe, In, Th, Sc, Hg, Ga, Lu, VO, Cu, Zn, Al, LA, Mn, Ca, Sr, Mg, Ni, Pb, Cd, or Co. In one embodiment, the cation of the metallic salt ($Me^+$) is not a Group I metal. In another embodiment, the metallic salt can comprise silver nitrate, $AgNO_3$.

In certain embodiments, the first endpoint and the second endpoint are determined based on one or more of measuring potential of ion-selective electrode, conductivity, temperature, color spectra, or electrochemical response.

The presently disclosed subject matter further provides apparatus for analyzing concentrations of silver ions ($Ag^+$) and complexing agent of an electrodeposition solution. In certain embodiments, the disclosed apparatus includes an analysis cell configured to contain an analysis solution, a sampling device, a precipitating agent injector, a titrator device configured to add a titrant solution of predetermined concentration to the analysis solution, a sensor for detecting a change in the analysis solution, and a controller. The controller can include one or more processors, and be configured to cause the sampling device to add a predetermined volume of the electrodeposition solution to the analysis solution; cause the precipitating agent injector to add a precipitating agent ($X^-$) having a predetermined concentration to the electrodeposition solution to cause a reaction between at least a portion of the precipitating agent ($X^-$) and substantially all of the silver ions ($Ag^+$) in the analysis solution such that the substantially all of silver ions ($Ag^+$) are precipitated out from the analysis solution as a precipitant (AgX); cause the titrator device to add a first amount of the titrant solution to the analysis solution to reach a first endpoint of titration, where the titrant has reacted with substantially all of the precipitating agent ($X^-$) remaining in the analysis solution; cause the titrator device to further add a second amount of the titrant solution to the analysis solution to reach a second endpoint of titration, where the titrant has reacted with substantially all of the complexing agent in the analysis solution; and determine the first endpoint and the second endpoint of titration based on an output of the sensor.

In certain embodiments, the apparatus can measure such changes in the analysis solution as potential of ion-selective electrode, conductivity, temperature, color, or electrochemical potential. In certain embodiments, the sensor of the disclosed apparatus can include an ion-selective electrode, a conductivity sensor, a temperature sensor, or a color spectral sensor. In certain embodiments, the apparatus can further include one or more optional inlets. Such optional inlets can be configured to introduce a diluent into the analysis cell. In certain embodiments, the diluent can include deionized water. In certain embodiments, the optional inlets can be configured to introduce an optional reagent into the analysis cell. In certain embodiments, the optional reagent can be nitric acid, which need not be added at a specific stoichiometric ratio to other reactants or to the electrodeposition solution.

The presently disclosed subject matter also provides a process control systems that control concentrations of silver ions ($Ag^+$) and complexing agent in an electrodeposition solution including at least tin ions, silver ions, and complexing agent. For example, in certain embodiments, a process control system can include an analyzer for determining the concentrations of silver ions ($Ag^+$) and complexing agent; a replenishing system for adding one or more agents to the electrodeposition solution; and one or more processors, coupled to the analyzer, the replenishing system, and a computer-readable medium containing executable instructions.

In certain embodiments, the executable instructions, when executed by the processors, can cause the process control system to determine the concentrations of silver ions (Ag+) and complexing agent by acquiring a sample of the electrodeposition solution, adding of a precipitating agent ($X^-$) having a predetermined concentration to the sample that causes the precipitation of substantially all of the silver ions ($Ag^+$) as a precipitant (AgX), titrating the precipitating agent ($X^-$) that remains in the sample with a metallic salt ($Me^+$); further titrating the complexing agent with a metallic salt ($Me^+$); and adding one or more reagents to the electrodeposition solution to maintain predetermined concentrations of silver ions ($Ag^+$) and complexing agent.

Further features and advantages of the presently disclosed subject matter will be apparent to those skilled in the art from the following detailed description, taken together with the accompanying drawings.

BRIEF DESCRIPTION OF THE DRAWINGS

FIG. 4 illustrates an exemplary apparatus for monitoring and measuring of the concentrations of silver ions and complexing agent of an electrodeposition solution.

DETAILED DESCRIPTION

The presently disclosed subject matter provides novel techniques for monitoring the concentrations of silver ions ($Ag^+$) and complexing agent in SnAg electrodeposition solution, analysis and process control using such methods. The presently disclosed methods can include a single, dual-step titration technique to determine the concentrations of silver ions and complexing agent in an electroplating bath.

Technical terms used in this document are used in a manner as generally known to those skilled in the art. The terms "electroplating," "plating," and "electrodeposition" refer to metal electrodeposition and are equivalent. The terms "electroplating bath" and "plating bath" are used interchangeably. The term "complexing agent" or "complexer" can refer to complexation of silver ions.

A "titrant solution" is a standard solution comprising a known concentration of a reagent called a "titrant" that chemically reacts with a "reactant" or "unknown species" whose concentration in a sample solution is to be determined. A "titration" is an analytical procedure based on stoichiometric reaction(s) involving repeated addition of known volume of titrant solution to an analysis solution (comprising the sample solution), coupled with monitoring of a physical or chemical property, such as temperature, potential of ion selective electrode, or concentration of an indicator species, e.g., titrant, unknown species, or additional reagents employed in the reaction, or the differential change of a physical or chemical property.

A "titration curve" is a plot of a physical or chemical property of a titration indicator species in an analysis solution, or a parameter correlated to such a property, as a function of the volume of titrant solution added to the analysis solution. It is typically more convenient to utilize a concentration parameter that is proportional to the concentration of the indicator species, especially when the indicator species participates in a complexation reaction involving competing complexing agents. The endpoint for the titration is typically determined from a curve feature corresponding to a rapid change in the concentration of the indicator species, such as a curve knee or inflection point. Detection of the titration endpoint can be facilitated by differentiating the titration curve, which converts an inflection point into a peak.

Figure 1:
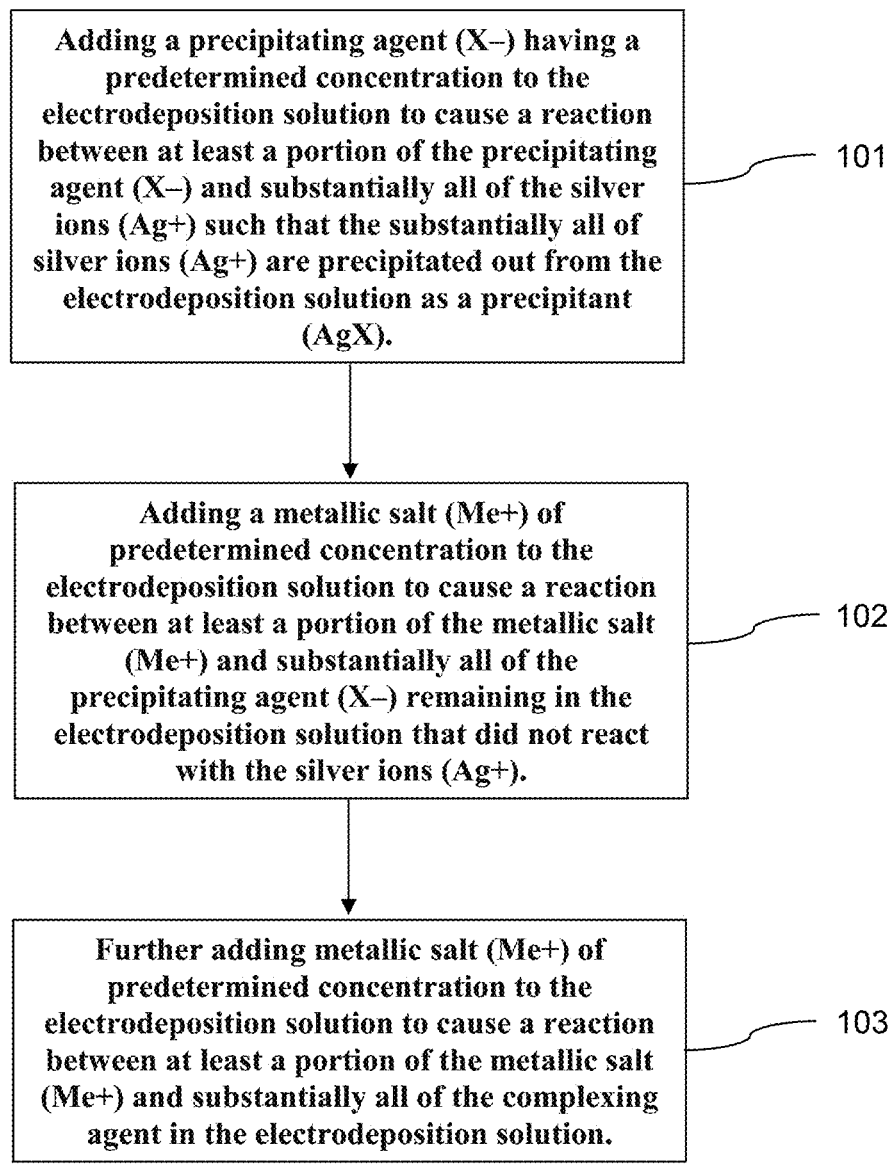
FIG. 1 depicts a method of monitoring the concentrations of silver ion ($Ag^+$) and complexing agent in tin-silver (SnAg) electrodeposition solutions according to one exemplary embodiment of the disclosed subject matter.

For the purpose of illustration and not limitation, FIG. 1 provides an exemplary method of monitoring the concentrations of silver ions ($Ag^+$) and complexing agent in a sample SnAg electrodeposition solution. The method can include adding a precipitating agent ($X^-$) having a predetermined concentration to the electrodeposition solution to cause a reaction between at least a portion of the precipitating agent ($X^-$) and substantially all of the silver ions ($Ag^+$) such that the substantially all of silver ions ($Ag^+$) are precipitated out from the electrodeposition solution as a precipitant (AgX) 101. Other optional reagents can also be added to the electrodeposition solution, such as deionized water (DIW) as a diluent or nitric acid ($HNO_3$) to aid reaction and sensor response. Next, a metallic salt ($Me^+$) of predetermined concentration is added to the electrodeposition solution to cause a reaction between at least a portion of the metallic salt ($Me^+$) and substantially all of the precipitating agent ($X^-$) remaining in the electrodeposition solution that did not react with the silver ions ($Ag^+$) 102. The process of 101 and 102 together comprise the back titration of silver ions. Measurement of this first endpoint can be used to calculate the concentration of silver ions in the sample electrodeposition solution. Further metallic salt ($Me^+$) of predetermined concentration is added to the electrodeposition solution to cause a reaction between at least a portion of the metallic salt (Me+) and substantially all of the complexing agent in the electrodeposition solution 103. The process of 103 is the titration of complexing agent. Measurement of this second endpoint can be used to calculate the concentration of complexing agent in the sample electrodeposition solution.

As used herein, the term "substantially all" means at least 85% of a particular amount or subject.

The phrase "predetermined concentration" refers to a known, target, or optimum concentration of a component in solution.

As used herein, the term "about" or "approximately" means within an acceptable error range for the particular value as determined by one of ordinary skill in the art, which will depend in part on how the value is measured or determined, i.e., the limitations of the measurement system. For example, "about" can mean a range of up to 20%, up to 10%, up to 5%, and or up to 1% of a given value.

As embodied herein, a sample of SnAg electrodeposition solution can be prepared using commercially available plating baths. For example, the sample can be prepared by diluting a predetermined amount of SnAg electrodeposition solution with deionized water. In certain embodiments, the dilution ratio can range from no dilution to 1:1000, from 1:2 to 1:500, from 1:5 to 1:250, or from 1:10 to 1:100. Additionally, nitric acid can be added to aid the reaction and sensor responses of an apparatus taking measurements of the electrodeposition solution.

In an exemplary embodiment, given a sample SnAg electrodeposition solution, where the concentration of silver ions and the concentration of a complexing agent are unknown, a precipitating agent, designated as $X^-$, of predetermined concentration, is added to the electrodeposition solution such that substantially all of the silver ions are precipitated out of solution as an insoluble compound, AgX.

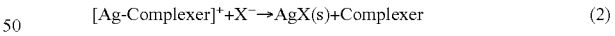

$$[\text{Ag-Complexer}]^+ + X^- \rightarrow \text{AgX(s)} + \text{Complexer} \qquad (2)$$

The precipitating agent $X^-$ should possess a stronger affinity for silver ions than the complexing agent, meaning when the electrodeposition solution contains both silver ions and complexing agent, the precipitant agent $X^-$ will always preferentially react with silver ions instead of complexing agent.

The anion of the precipitating agent $X^-$ can be selected from the group consisting of $Cl^-$, $Br^-$, $I^-$, $PO_4^{3-}$, $CN^-$, $C_2O_4^{2-}$, $S^{2-}$, $F^-$, $SO_4^{2-}$, $CO_3^{2-}$, or $BH_4^-$. In a preferred embodiment, the precipitating agent comprises potassium iodide, KI.

As shown in reaction (2), when the silver ions are converted to insoluble precipitant form, substantially all of the complexing agent bound to silver ions are released into solution. Next, the electrodeposition solution containing freed complexing agent is titrated with a metallic salt, designated as $Me^+$. Similarly, precipitant agent $X^-$ should possess a stronger affinity for the metallic salt $Me^+$ than for the complexing agent, such that the precipitant agent $X^-$ will always preferentially react with metallic salt $Me^+$ instead of complexing agent. The following reaction dominates until any or substantially all excess precipitating agent $X^-$ is neutralized.

$$X^- + Me^+ \rightarrow MeX \quad (3)$$

The cation of the metallic salt $Me^+$ can be selected from the group consisting of Ag, Fe, In, Th, Sc, Hg, Ga, Lu, VO, Cu, Zn, Al, LA, Mn, Ca, Sr, Mg, Ni, Pb, Cd, or Co. The cation of the metallic salt can also not be a Group I metal. In a preferred embodiment, the metallic salt comprises silver nitrate, $AgNO_3$.

The first endpoint of the back titration process, comprising of reactions (2) and (3) together, is inversely correlated to the silver ion concentration in solution. The more silver ions present in the sample electrodeposition solution, the smaller amount of precipitating agent $X^-$ will remain after all the silver ions are precipitated out as AgX. Thus, less metallic salt $Me^+$ will be required to react with the remaining precipitating agent $X^-$ still in the electrodeposition solution.

Figure 2:
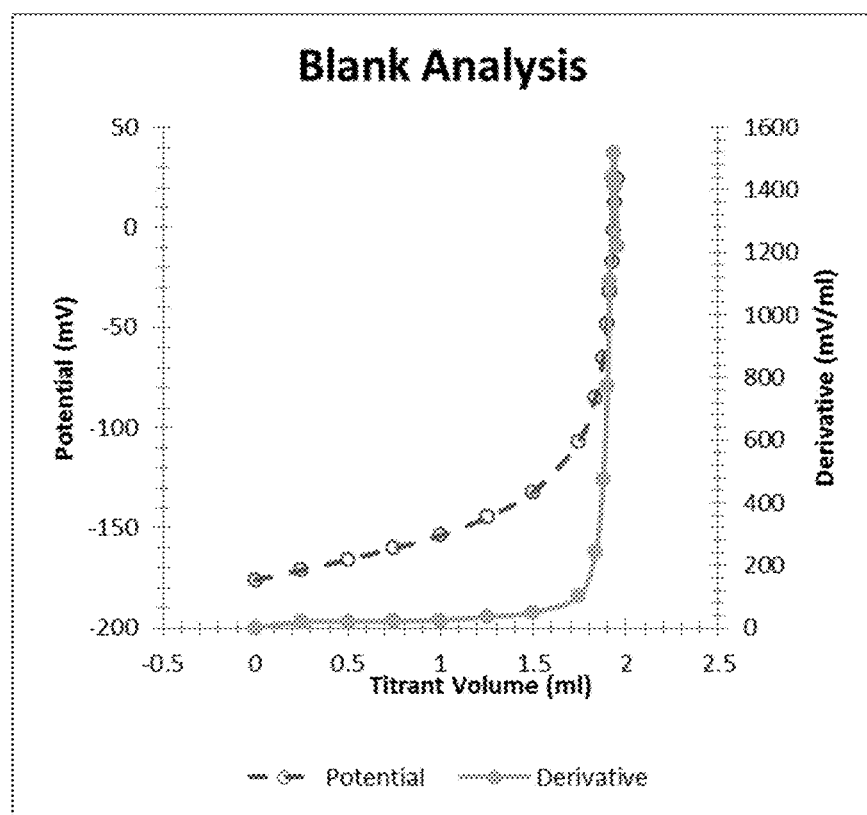
FIG. 2 shows a titration curve and differentiated titration curve of the potential of a silver ion-selective electrode as a function of the volume of metallic salt ($Me^+$) titrant solution. This (first) titration endpoint shows measurement of the concentration of a blank sample solution containing no silver ions in the plating bath.

FIG. 2 shows a titration curve and differentiated titration curve of the potential of a silver ion-selective electrode as a function of the volume of metallic salt titrant solution. This (first) titration endpoint is indicated by the asymptotic and drastic increase in the derivative curve. The first endpoint provides a measure of and can be used to calculate the silver ion concentration in the plating bath. In FIG. 2, a blank sample solution, containing no silver ions, is used. Thus, precipitating agent $X^-$ was not consumed as per reaction (2), and only consumed in reaction (3) with metallic salt $Me^+$.

Next, after the precipitating agent $X^-$ is neutralized from reaction (3), the same metallic salt $Me^+$ is further added to the sample electrodeposition solution until substantially all the complexing agent is reacted.

$$\text{Complexer} + Me^+ \rightarrow [Me\text{-Complexer}]^+ \quad (4)$$

This second endpoint of the titration in reaction (4) directly correlates to the concentration of complexing agent. If more complexing agent is present, the more metallic salt $Me^+$ is required to bind to it.

Figure 3:
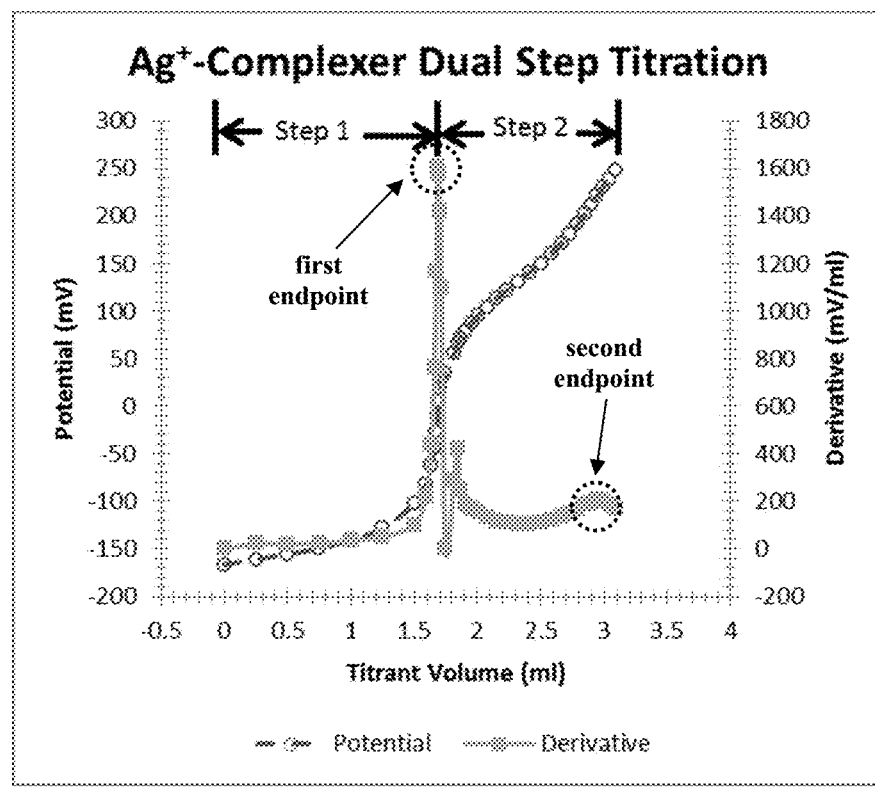
FIG. 3 shows a dual-step titration curve and differentiated dual-step titration curve of the potential of a silver ion-selective electrode as a function of the volume of metallic salt titrant solution. The first endpoint provides a measure of the silver ion concentration in the plating bath, and the second endpoint provides a measure of the total complexing agent concentration in the plating bath.

FIG. 3 shows a titration curve and differentiated titration curve of the potential of a silver ion-selective electrode as a function of the volume of metallic salt ($Me^+$) titrant solution. In FIG. 3, the first endpoint provides a measure of the silver ion concentration, and the second endpoint provides a measure of the total complexing agent concentration in the plating bath. FIG. 3 represents the single, dual-step titration method presently disclosed.

The first and second endpoints can be determined, but not limited to, changes based on potential of ion selective electrode, conductivity, temperature, spectra (e.g., color), or electrochemical response. For example, endpoints can be measured using silver ion-selective electrodes.

The presently disclosed subject matter can include an apparatus for determining the concentrations of silver ions and complexing agent in an electroplating bath. In certain embodiments, an apparatus, such as an analyzer, can be used to monitor and measure the concentrations of silver ions and complexing agent in a Sn—Ag electrodeposition solution.

FIG. 4 shows a non-limiting exemplary diagram of an analyzer of the presently disclosed subject matter. In certain embodiments, analyzer 400 includes an analysis cell 405 for containing an analysis solution 408, a sampling device 401 for adding a predetermined volume of sample of the electrodeposition solution into analysis cell 405, a precipitating agent injector 402 for adding a predetermined volume of a solution with a known concentration of a precipitating agent into analysis cell 405, a titrator device 403 for adding an aliquot of a known volume of a titrant solution to analysis cell 405, and a sensor 409 for monitoring properties of analysis solution 408. In certain embodiments, analyzer 400 can further include a controller 410 in communication with at least one of analysis cell 405, sampling device 401, precipitating agent injector 402, titrator device 403, and sensor 409. In certain embodiments, analyzer 400 can further include one or more optional inlets 404 for introducing additional reagents. In certain embodiments, analyzer 400 can further include a solution stirring device 406 for stirring analysis solution 408. In certain embodiments, analyzer 400 can further include a cell cleaning device 407 for reducing cross-contamination between analysis.

The design of analysis cell 405 can depend on various considerations, including analysis methods, precision requirements, and level of automation. Depending on need of the application, analysis cell 405 can be of different capacity ranging from a few milliliters to a few liters. The sampled amount of electrodeposition solution can vary accordingly. Analysis cell 405 can be a simple beaker or a closed cell. Analysis cell 405 can be made from various chemical resistant materials including glass, plastic, and stainless steel. Analysis cell 405 can be of different shapes that facilitate the analysis operations. For example, the analysis cell 405 can be cylindrical. In certain embodiment analysis cell 405 can include an optical window to be used in conjunction with an optical spectroscopic sensor.

In certain embodiments, sampling device 401, precipitating agent injector 402, titrator device 403, and optional inlets 404 can each comprise a suitable solution metering device. Such a solution metering device can include a metering pump, a syringe, or other devices known in the art. In certain embodiment, precipitating agent injector 402, titrator device 403, and optional inlets 404 can each include a pump and/or valve that controls delivery from a pressurized supply.

Sensor 409 can include various types of sensor for monitor changes in analysis solution 408. Such changes can include electrochemical potential, conductivity, temperature, or color changes. In certain embodiments, sensor 409 can be an ion selective electrode, conductivity meter, thermometer, or UV/visible spectrometer. In certain embodiments, sensor 409 can include a silver ion-selective electrode.

Solution stirring device 406 can be used to stir analysis solution 408 to improve solution uniformity and analysis precision. In certain embodiments, solution stirring device 406 can include a magnetic stirrer coupled a with a magnetic stir bar. In certain embodiments, solution stirring device 406 can include an impellor driven by an electrical stirring motor, a gas bubbler, an ultrasonic wave generator, or a solution circulator.

One or more optional inlets 404 can be used to introduce additional reagents into the analysis solution 408. In certain embodiments, the additional reagents can include deionized water as diluent. In certain embodiments, the additional reagents can include nitric acid, $HNO_3$, to aid in reaction and sensor response, which does not need to be in a stoichiometric ratio with other reagents or with the electrodeposition solution.

In certain embodiments, cell cleaning device 407 can rinse analysis cell 405 with purified water (pumped into the cell) and collects the rinse water for subsequent disposal. In certain embodiments, cell cleaning device 407 can further blow dry analysis cell 405 to further reduce cross-contamination between subsequently analyses.

In certain embodiments, analyzer 400 further include controller 410. In certain embodiments, controller 410 is configured to communicate with or control one or more components including analysis cell 405, sampling device 401, precipitating agent injector 402, titrator device 403, sensor 409, stirring device 406, and optional inlets 404. In certain embodiments, controller 410 can include one or more processors, coupled to a computer-readable medium containing executable instructions that can be executed by the processors.

In certain embodiments, the controller can be configured to cause sampling device 401 to add a predetermined volume of the electrodeposition solution to analysis cell 405; cause precipitating agent injector 402 to add a precipitating agent ($X^-$) having a predetermined concentration to the electrodeposition solution to cause a reaction between at least a portion of the precipitating agent ($X^-$) and substantially all of the silver ions ($Ag^+$) in analysis solution 408 such that substantially all of silver ions ($Ag^+$) are precipitated out from the analysis solution 408 as a precipitant (AgX); cause titrator device 403 to add an amount of the titrant solution to analysis solution 408 to reach a first endpoint of titration, where the titrant has reacted with substantially all of the precipitating agent ($X^-$) remaining in analysis solution 408; cause titrator device 403 to further add another amount of the titrant solution to the analysis solution to reach a second endpoint of titration where the titrant has reacted with substantially all of the complexing agent in analysis solution 408; determine the first endpoint and the second endpoint of titration based on an output of sensor 409; and calculate concentrations of silver ions ($Ag^+$) and complexing agent in the electrodeposition solution.

In certain embodiments, controller 410 is further configured to control solution stirring device 406. In certain embodiments, controller 410 is configured to control optional inlets 404. In certain embodiments, controller 410 is configured to control cell cleaning device 407.

In certain embodiments, analyzer 400 of the presently disclosed subject matter is not limited to monitoring and measurements of silver ions and complexing agent. In certain embodiments, analyzer 400 can also measure and monitor, for example, but by no means as a limitation, the amounts of tin(II) ($Sn^{2+}$) or tin(IV) ($Sn^{4+}$) ions, amounts of other acid or acidic reagents, pH, amounts of primary polarizer, and amounts of secondary polarizer, and optionally, amounts of antioxidant, tin ion breakdown contaminant, and leached photoresist contaminant.

The presently disclosed subject matter can include a process control system. For example, but by no means as a limitation, such a process control system can include an analyzer as disclosed above and a replenishing system to maintain steady concentrations of silver ions and complexing agent in an electroplating bath. During electroplating, tin ions, silver ions, complexing agent, and other plating bath components are depleted or break down over time and require replenishing in order to maintain a consistent electrodeposition process. In certain embodiments, the replenishing system replenishes the electroplating bath based on the concentrations of the silver ions and complexing agent determined by the analyzer.

In one embodiment, the process control system can include an analyzer for determining the concentrations of silver ions and complexing agent in an electrodeposition solution, a replenishing system for adding one or more reagents to the electrodeposition solution; one or more processors coupled to the analyzer and replenishing system; and a computer-readable medium containing executable instructions. When executed by the one or more processors, the executable instructions can cause the process control system to determine the concentrations of silver ions and complexing agent by acquiring a sample of the electrodeposition solution, adding a precipitating agent of predetermined concentration to precipitate substantially all of the silver ions as a precipitant AgX, titrating the precipitating agent that remains in the sample with a metallic salt, further titrating the complexing agent with metallic salt, and adding one or more reagents to the electrodeposition solution to maintain a predetermined concentration of silver ions and complexing agent.

The presently disclosed subject matter will be better understood by reference to the following Examples, which are provided as exemplary of the present disclosure and not by way of limitation.

EXAMPLE 1

Monitoring $Ag^+$ and Complexing Agent Concentrations Via Dual-Step Titration

In this example, a test sample Sn—Ag electrodeposition solution contained the following concentrations: 50 g/l of tin(II) ions ($Sn^{2+}$), 150 g/l of methanesulfonic acid (MSA), 0.5 g/l of silver ions ($Ag^+$), and 5 g/l of thiourea complexing agent. The tin ions and silver ions were added into the electrodeposition solution as MSA salts.

A test sample of 0.5 ml of the electrodeposition solution was first treated with 2 ml of 0.01 normality potassium iodide, KI. Then the test sample was titrated with 0.01 normality silver nitrate, $AgNO_3$. Potential was measured by a silver ion-selective electrode. Data was collected using a Qualilab® QL-100EZ benchtop analyzer manufactured by ECI Technology.

FIG. 3 represents the titration curve and differentiated titration curve of the potential of the silver ion-selective electrode as a function of the volume of $AgNO_3$.

EXAMPLE 2

Comparison of Prior Art Method and Present Disclosure Method

A series of analyses were performed using a certain "free complexer" method currently known in the art and compared to an example in accordance with the presently disclosed subject matter. In the "free complexer" method, total complexing agent concentration is calculated based on the amount of free (unreacted) complexer concentration in solution plus the amount of silver ion concentration, using a predefined ratio or binding factor. See reaction (5).

In Example 2, three solutions were each analyzed ten times (i.e., 10 trials) under the "free complexer" method and the method of the present disclosure. The Sn—Ag electrodeposition solution used was SolderOn™ BP TS 6000, a commercially available electrolyte plating bath manufactured by Dow®. The concentrations of silver ions and complexing agent were varied in the electrodeposition solutions as follows:

Solution 1: 0.2 g/l of $Ag^+$ and 20 ml/l of Complexer
Solution 2: 0.3 g/l of $Ag^+$ and 30 ml/l of Complexer
Solution 3: 0.4 g/l of $Ag^+$ and 40 ml/l of Complexer Data was collected using Quali-Fill™ QFDS-1000E automatic chemical management system manufactured by ECI Technology. The results were tabulated as follows:

TABLE I

Free Complexer (Prior Art)

| Data Points | Solution 1 | Solution 2 | Solution 3 |
|---|---|---|---|
| 1 | 10.85 | 15.39 | 20.76 |
| 2 | 11.68 | 16.08 | 21.34 |
| 3 | 11.72 | 15.34 | 21.25 |
| 4 | 11.38 | 15.33 | 20.93 |
| 5 | 11.91 | 16.05 | 20.87 |
| 6 | 11.63 | 15.77 | 20.68 |
| 7 | 10.84 | 15.39 | 20.92 |
| 8 | 11.67 | 15.57 | 20.91 |
| 9 | 11.09 | 15.53 | 20.83 |
| 10 | 11.15 | 15.51 | 21.04 |
| Average | 11.39 | 15.60 | 20.95 |
| Expected | 11.00 | 16.50 | 22.00 |
| Accuracy | 3.56 | −5.48 | −4.76 |
| StDev | 0.39 | 0.28 | 0.21 |
| RSD | 3.39 | 1.79 | 0.98 |

TABLE II

Corresponding Ag⁺ (Prior Art)

| Data Points | Solution 1 | Solution 2 | Solution 3 |
|---|---|---|---|
| 1 | 0.205 | 0.296 | 0.4 |
| 2 | 0.211 | 0.298 | 0.4 |
| 3 | 0.209 | 0.295 | 0.4 |
| 4 | 0.206 | 0.295 | 0.397 |
| 5 | 0.212 | 0.296 | 0.401 |
| 6 | 0.209 | 0.295 | 0.401 |
| 7 | 0.206 | 0.295 | 0.401 |
| 8 | 0.217 | 0.295 | 0.401 |
| 9 | 0.208 | 0.297 | 0.402 |
| 10 | 0.206 | 0.297 | 0.402 |
| Average | 0.21 | 0.30 | 0.40 |
| Expected | 0.20 | 0.30 | 0.40 |
| Accuracy | 4.45 | −1.37 | 0.12 |
| StDev | 0.00 | 0.00 | 0.00 |
| RSD | 1.75 | 0.37 | 0.36 |

In Tables I and II above, as well as Tables III, IV, and V below, the 10 trials of each of the three solution concentrations are tabulated. An "Average" is calculated for each solution based on the 10 separate trials. This "Average" is compared to the "Expected" target amount, and a subsequent level of "Accuracy" as a percentage above (+) or below (−) target. The standard deviation ("StDev") and relative standard deviation ("RSD") are accordingly tabulated.

Given the amount of free complexer and measured silver ions, the total complexer in the electrodeposition solution can be calculated by a mathematical relationship as follows:

$$\text{Total Complexer} = \text{Free Complexer} + \text{Binding Factor} \times \text{Measured Ag Ions} \quad (5)$$

TABLE III

Total Complexer (Prior Art)

| Data Points | Solution 1 | Solution 2 | Solution 3 |
|---|---|---|---|
| 1 | 20.075 | 28.71 | 38.76 |
| 2 | 21.175 | 29.49 | 39.34 |
| 3 | 21.125 | 28.615 | 39.25 |
| 4 | 20.65 | 28.605 | 38.795 |
| 5 | 21.45 | 29.37 | 38.915 |
| 6 | 21.035 | 29.045 | 38.725 |
| 7 | 20.11 | 28.665 | 38.965 |
| 8 | 21.435 | 28.845 | 38.955 |
| 9 | 20.45 | 28.895 | 38.92 |
| 10 | 20.42 | 28.875 | 39.13 |
| Average | 20.79 | 28.91 | 38.98 |
| Expected | 20.00 | 30.00 | 40.00 |
| Accuracy | 3.96 | −3.63 | −2.56 |
| StDev | 0.52 | 0.31 | 0.21 |
| RSD | 2.49 | 1.06 | 0.53 |

Using the methods disclosed by the present subject matter, no additional calculation step was required to determine the total complexer concentration. The results were as follows:

TABLE IV

Corresponding Ag⁺ (New Method)

| Data Points | Solution 1 | Solution 2 | Solution 3 |
|---|---|---|---|
| 1 | 0.203 | 0.304 | 0.403 |
| 2 | 0.203 | 0.302 | 0.401 |
| 3 | 0.201 | 0.294 | 0.401 |
| 4 | 0.201 | 0.304 | 0.399 |
| 5 | 0.209 | 0.304 | 0.4 |
| 6 | 0.199 | 0.3 | 0.397 |
| 7 | 0.196 | 0.306 | 0.391 |
| 8 | 0.211 | 0.303 | 0.398 |
| 9 | 0.211 | 0.304 | 0.395 |
| 10 | 0.211 | 0.308 | 0.402 |
| Average | 0.20 | 0.30 | 0.40 |
| Expected | 0.20 | 0.30 | 0.40 |
| Accuracy | 2.25 | 0.97 | −0.33 |
| StDev | 0.01 | 0.00 | 0.00 |
| RSD | 2.72 | 1.25 | 0.91 |

TABLE V

Total Complexer (New Method)

| Data Points | Solution 1 | Solution 2 | Solution 3 |
|---|---|---|---|
| 1 | 20.63 | 30.87 | 40.17 |
| 2 | 20.3 | 30.05 | 40.07 |
| 3 | 20.73 | 30.17 | 40.2 |
| 4 | 20.68 | 30.55 | 39.96 |
| 5 | 20.16 | 30.69 | 40.21 |
| 6 | 20.52 | 30.51 | 39.27 |
| 7 | 21.06 | 29.92 | 40.27 |
| 8 | 20.67 | 29.88 | 39.33 |
| 9 | 20.59 | 29.67 | 39.03 |
| 10 | 20.38 | 29.64 | 39.21 |
| Average | 20.27 | 30.20 | 39.77 |
| Expected | 20.00 | 30.00 | 40.00 |
| Accuracy | 1.35 | 0.65 | −0.57 |
| StDev | 0.25 | 0.44 | 0.50 |
| RSD | 1.24 | 1.44 | 1.25 |

A summary of the performance of each method in Table VI below indicated the methods of the present disclosure yielded better accuracy in measuring concentrations of both silver ions and complexing agent. (Accuracy spread refers to the difference in accuracy between the three test solutions. While a constant shift in accuracy can be compensated through a constant bias correction, a variable shift is difficult to counterbalance.)

TABLE VI

| | Prior Art | | Invention | |
|---|---|---|---|---|
| Component | $Ag^+$ | Total Complexer | $Ag^+$ | Total Complexer |
| Accuracy, % | −1.37 . . . +4.45% | −2.56 . . . +3.96% | −0.33 . . . +2.25% | −0.57 . . . +1.35% |
| Accuracy Spread, % | 5.82% | 6.52% | 2.58% | 1.92% |
| Relative Standard Deviation, % | 0.36-1.75% | 0.53-2.49% | 0.91-2.72% | 1.24-1.44% |

Thus, the present disclosure provides a superior analytical performance for monitoring the concentration of complexing agent, and at least equal or better performance for monitoring the concentration of silver ions.

In addition to the various embodiments depicted and claimed, the disclosed subject matter is also directed to other embodiments having other combinations of the features disclosed and claimed herein. As such, the particular features presented herein can be combined with each other in other manners within the scope of the disclosed subject matter such that the disclosed subject matter includes any suitable combination of the features disclosed herein. The foregoing description of specific embodiments of the disclosed subject matter has been presented for purpose of illustration and description. It is not intended to be exhaustive or to limit the disclosed subject matter to those embodiments disclosed.

It will be apparent to those skilled in the art that various modifications and variations can be made in the systems and methods of the disclosed subject matter without departing from the spirit or scope of the disclosed subject matter. Thus, it is intended that the disclosed subject matter include modifications and variations that are within the scope of the appended claims and their equivalents.

What is claimed is:

1. A method of monitoring concentrations of silver ions ($Ag^+$) and complexing agent in an electrodeposition solution including at least tin ions, silver ions, and complexing agent, comprising the steps of:
    (a) adding a precipitating agent ($X^-$) having a predetermined concentration to the electrodeposition solution to cause a reaction between at least a first portion of the precipitating agent ($X^-$) and substantially all of the silver ions ($Ag^+$) such that the substantially all of the silver ions ($Ag^+$) are precipitated out from the electrodeposition solution as a precipitant (AgX) and such that at least a second portion of the precipitating agent ($X^-$) that did not react with the silver ions ($Ag^+$) remains in the electrodeposition solution, wherein the second portion of the precipitating agent ($X^-$) did not react with the silver ions ($Ag^+$) and remains in the electrodeposition solution;
    (b) adding a metallic salt ($Me^+$) of predetermined concentration to the electrodeposition solution to cause a reaction between at least a portion of the metallic salt ($Me^+$) and substantially all of the second portion of the precipitating agent ($X^-$) remaining in the electrodeposition solution that did not react with the silver ions ($Ag^+$);
    (c) measuring a first endpoint of back titration of the silver ions ($Ag^+$);
    (d) further adding metallic salt ($Me^+$) of predetermined concentration to the electrodeposition solution to cause a reaction between at least a portion of the metallic salt ($Me^+$) and substantially all of the complexing agent in the electrodeposition solution; and
    (e) measuring a second endpoint of titration of the complexing agent.

2. The method of claim 1, further comprising calculating the concentration of silver ions ($Ag^+$) originally in the electrodeposition solution based on the first endpoint.

3. The method of claim 1, further comprising calculating the concentration of complexing agent originally in the electrodeposition solution based on the second endpoint.

4. The method of claim 1, wherein the precipitating agent has a stronger affinity for silver ions than the complexing agent.

5. The method of claim 1, wherein the anion of the precipitating agent ($X^-$) is selected from the group consisting of $Cl^-$, $Br^-$, $I^-$, $PO_4^{3-}$, $CN^-$, $C_2O_4^{2-}$, $S^{2-}$, $F^-$, $SO_4^{2-}$, $CO_3^{2-}$, or $BH_4^-$.

6. The method of claim 1, wherein the precipitating agent comprises potassium iodide, KI.

7. The method of claim 1, wherein the cation of the metallic salt ($Me^+$) is selected from the group consisting of $Ag^+$, $Fe^{2+}$, $Fe^{30}$, $In^{3+}$, $Hg^+$, $Hg^{2+}$, $Ga^{2+}$, $Ga^{3+}$, $VO^{2+}$, $Cu^+$, $Cu^{2+}$, $Zn^{2+}$, $Al^{3+}$, $La_{3+}$, $Mn^{2+}$, $Ca^{2+}$, $Sr^{2+}$, $Mg^{2+}$, $Ni^{2+}$, $Ni^{3+}$, $Pb^{2+}$, $Cd^{2+}$, $Co^{2+}$, or $Co^{3+}$.

8. The method of claim 1, wherein the cation of the metallic salt ($Me^+$) is not a Group I metal.

9. The method of claim 1, wherein the metallic salt comprises silver nitrate, $AgNO_3$.

10. The method of claim 1, wherein the first endpoint and the second endpoint are determined based on one or more of measuring potential of ion-selective electrode, conductivity, temperature, color spectra, or electrochemical response.

* * * * *

UNITED STATES PATENT AND TRADEMARK OFFICE
CERTIFICATE OF CORRECTION

PATENT NO. : 10,407,795 B2
APPLICATION NO. : 15/353424
DATED : September 10, 2019
INVENTOR(S) : Vishal Parekh et al.

It is certified that error appears in the above-identified patent and that said Letters Patent is hereby corrected as shown below:

In the Specification

In Column 3, Line 38, "VO" should read -- V --

In Column 3, Line 38, "Lu" should be removed

In Column 3, Line 39, "LA" should read -- La --

In Column 7, Line 10, "VO" should read -- V --

In Column 7, Line 10, "Lu" should be removed

In Column 7, Line 11, "LA" should read -- La --

In the Claims

In Claim 7, at Column 14, Line 45, "$Fe^{30}$" should read -- $Fe^{3+}$ --

In Claim 7, at Column 14, Line 46, "$La_{3+}$" should read -- $La^{3+}$ --

Signed and Sealed this
Nineteenth Day of November, 2019

Andrei Iancu
*Director of the United States Patent and Trademark Office*